United States Patent
Sekiguchi et al.

(10) Patent No.: US 11,795,449 B2
(45) Date of Patent: Oct. 24, 2023

(54) NUCLEIC ACID COLLECTION COLUMN

(71) Applicant: Toray Industries, Inc., Tokyo (JP)

(72) Inventors: Shota Sekiguchi, Kamakura (JP); Takahiro Motoshiromizu, Kamakura (JP); Masateru Ito, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 335 days.

(21) Appl. No.: 17/283,624

(22) PCT Filed: Oct. 30, 2019

(86) PCT No.: PCT/JP2019/042599
§ 371 (c)(1),
(2) Date: Apr. 8, 2021

(87) PCT Pub. No.: WO2020/090900
PCT Pub. Date: May 7, 2020

(65) Prior Publication Data
US 2021/0340522 A1    Nov. 4, 2021

(30) Foreign Application Priority Data

Oct. 31, 2018 (JP) ................................ 2018-205482

(51) Int. Cl.
C12N 15/00 (2006.01)
C12N 15/10 (2006.01)
B01D 15/20 (2006.01)

(52) U.S. Cl.
CPC ....... *C12N 15/1006* (2013.01); *B01D 15/206* (2013.01)

(58) Field of Classification Search
CPC ................................................ C12N 15/1006
(Continued)

(56) References Cited

U.S. PATENT DOCUMENTS 6,277,648 B1    8/2001    Colpan
8,247,545 B1    8/2012    Colpan
(Continued)

FOREIGN PATENT DOCUMENTS

EP    2 725 102 A1    4/2014
JP    2001-95572 A    4/2001
(Continued)

OTHER PUBLICATIONS

Extended European Search Report dated Jul. 21, 2022, of counterpart European Patent Application No. 19880900.6.
(Continued)

*Primary Examiner* — Christine T Mui
*Assistant Examiner* — Emily R. Berkeley
(74) *Attorney, Agent, or Firm* — DLA Piper LLP (US)

(57) ABSTRACT

This disclosure relates to a nucleic acid collection column that collects a nucleic acid from a liquid sample containing the nucleic acid. The nucleic acid collection column includes a sample injection portion having an opening into which the liquid sample containing the nucleic acid is injected, a support adsorption portion that houses a support for adsorbing the nucleic acid and in which the nucleic acid is adsorbed on the support, and a discharge portion that discharges a liquid passed through the support adsorption portion. The support includes aluminum oxide having a surface where a water-soluble neutral polymer is adsorbed. A space that houses the support in the support adsorption portion has a cylindrical shape, and has a volume of 0.13 µL or more and 13.5 µL or less. An aspect ratio ($d_1/d_2$) of the space satisfies $1.0 \le d_1/d_2 < 15.0$.

3 Claims, 3 Drawing Sheets

(58) Field of Classification Search
USPC .......................................................... 422/527
See application file for complete search history.

(56) References Cited

U.S. PATENT DOCUMENTS

| | | |
|---|---|---|
| 2001/0047966 A1 | 12/2001 | Colpan |
| 2018/0051274 A1 | 2/2018 | Sekiguchi et al. |
| 2019/0203200 A1 | 7/2019 | Nakagawa et al. |

FOREIGN PATENT DOCUMENTS

| | | |
|---|---|---|
| WO | 2016/052386 A1 | 4/2016 |
| WO | 2016/152763 A1 | 9/2016 |
| WO | 2018/052011 A1 | 3/2018 |

OTHER PUBLICATIONS

Notice of Reasons for Refusal dated Aug. 22, 2023, of counterpart Japanese Patent Application No. 2019-561200, along with an English translation.

NUCLEIC ACID COLLECTION COLUMN

TECHNICAL FIELD

This disclosure relates to a nucleic acid collection column.

BACKGROUND

Development of experimental techniques using nucleic acids has enabled a novel gene search and analysis of the gene. The human genome has been analyzed to identify a disease such as cancer, and the genome of pathogen has been analyzed to identify infection of the pathogen. Thus, a screening test and a clinical test using gene analysis have been performed in clinical sites.

For gene analysis, a step of collecting a nucleic acid from a sample containing a nucleic acid is performed. At that time, a column filled with a support to adsorb a nucleic acid is used. For example, International Publication WO 2016/052386 discloses a column filled with a support. In WO '386, a space to be filled with a support is a cylindrical space the height of which is smaller than the diameter of an opening (a top surface or a lower surface), that is, a wide and thin space.

After a nucleic acid is adsorbed on the support in the aforementioned column, the adsorbed nucleic acid is separated from the support and eluted into an eluent. To efficiently collect the nucleic acid and improve the collection rate, increases in an adsorption ratio on the support and elution in the eluent are required.

For analysis of genetic information of a nucleic acid using a solution containing the collected nucleic acid, a nucleic acid concentration equal to or more than a certain concentration is required. Therefore, it is necessary that a nucleic acid be collected by using a small amount of eluent. In particular, in the clinical sites and the like, there is a need for efficiently collecting a nucleic acid and performing a test even when the amount of a sample containing a nucleic acid is small.

In view of the circumstances, it could be helpful to provide a nucleic acid collection column capable of efficiency collecting a nucleic acid. The nucleic acid collection column makes it possible to collect a nucleic acid with a small amount of eluent, especially from a small amount of sample containing a nucleic acid.

SUMMARY

We thus provide a nucleic acid collection column for collecting a nucleic acid from a liquid sample containing the nucleic acid. The nucleic acid collection column includes: a sample injection portion having an opening into which the liquid sample containing the nucleic acid is injected; a support adsorption portion configured to house a support for adsorbing the nucleic acid, the nucleic acid being adsorbed on the support in the support adsorption portion; and a discharge portion configured to discharge a liquid passed through the support adsorption portion. The support includes aluminum oxide having a surface where a water-soluble neutral polymer is adsorbed, a space for housing the support in the support adsorption portion has a cylindrical shape, and has a volume of 0.13 µL or more and 13.5 µL or less, and an aspect ratio ($d_1/d_2$) of the space satisfies $1.0 \leq d_1/d_2 < 15.0$, where $d_1$ is a length in an axial direction of the space, and $d_2$ is a diameter in a direction orthogonal to the axial direction.

The discharge portion includes a support-holding sheet configured to hold the support housed in the support adsorption portion, and a ring fixing the support-holding sheet, and the ring has an internal diameter that is larger than a diameter of an opening of the support adsorption portion on a side of the discharge portion.

The support has a particle diameter of 10 µm or more and 60 µm or less.

According to our nucleic acid collection column, nucleic acids can be collected with high efficiency. In particular, the nucleic acid collection column provides the effect of collecting a high concentration of nucleic acid from a small amount of a sample.

REFERENCE SIGNS LIST

1 Nucleic acid collection column
10 Body
11 Sample injection portion
12 Support adsorption portion
13 Discharge portion
121 Support
131 Support-holding sheet
132 Ring

DETAILED DESCRIPTION

Hereinafter, aspects of collection columns and methods will be described in detail with the drawings. This disclosure, however, is not limited to the following examples. The drawings referred to in the following description only schematically illustrate shapes, sizes, and positional relations enough to understand the content. Therefore, the sizes, shapes, and positional relations are not limited to those exemplified in the drawings. In the description of the drawings, the same portions are denoted with the same reference symbols.

Our nucleic acid collection column is used to collect a nucleic acid from a sample containing a nucleic acid. Examples of the nucleic acid include RNA, DNA, RNA/DNA (chimera), and an artificial nucleic acid. Examples of DNA include cDNA, microDNA (miDNA), genome DNA, synthetic DNA, cell-free DNA (cfDNA), circulating tumor DNA (ctDNA), and mitochondrial DNA (mtDNA). Examples of RNA include totalRNA, mRNA, rRNA, miRNA, siRNA, snoRNA, snRNA, or non-coding RNA, or precursors thereof, and synthetic RNA.

Examples of the sample containing a nucleic acid include biological samples. As a biological sample, a cell-derived sample such as a cultured cell, a culture broth of a cultured cell, a tissue sample, or a specimen, a sample derived from a microorganism such as a bacterium or a virus, a sample derived from an animal including human such as a body fluid or feces, or a solution containing a compound having a biological function such as a protein, a sugar, or a lipid, can be used, in addition to the nucleic acid. The biological sample is not limited to them. The biological sample is preferably a cultured cell or a body fluid, and further preferably blood or urine. Blood includes whole blood, plasma, serum, and hemocyte.

The sample containing a nucleic acid may be subjected to the following treatment, if necessary. This is because the nucleic acid in the biological sample is often encapsuled in a compound such as a cell membrane, a cell wall, a vesicle, a liposome, a micelle, a ribosome, a histone, a nuclear membrane, a mitochondrion, a virus capsid, an envelope, an endosome, or an exosome or they often interact with each other. To collect the nucleic acid at a high yield, a treatment that releases the nucleic acid from them may be carried out.

Specifically, the following treatment is carried out to improve the collection efficiency of a nucleic acid from a sample containing *Escherichia coli*. For example, to the biological sample containing *Escherichia coli*, a mixed solution of 0.2 M sodium hydroxide and 1% sodium dodecyl sulfate (SDS) is added (alkaline denaturation method), or a 10% sarkosyl solution is added (sarkosyl non-denaturation method using sarkosyl). Lysozyme may be further added to the solution. The sample may also be treated with proteinase K at 37° C. for 1 hour. In addition, an ultrasonic wave treatment may be carried out.

When the sample contains a yeast, the following treatment may be carried out to improve the collection efficiency of a nucleic acid. For example, 10% SDS may be added after a treatment with a yeast cell wall lytic enzyme available from SEIKAGAKU CORPORATION or NACALAI TESQUE, INC.

When the sample containing a nucleic acid contains a cell, the following treatment may be carried out to improve the collection efficiency of a nucleic acid. Specifically, 1% SDS is added to the sample containing a cell. In addition, guanidium chloride, guanidine thiocyanate, urea, or the like may be added in a final concentration of 4 M or more. To this solution, sarkosyl may also be added in a concentration of 0.5% or more. Mercaptoethanol may also be added in a concentration of 50 mM or more.

In the aforementioned treatments, an inhibitor for a nuclease may be added to suppress degradation of a nucleic acid. Examples of the inhibitor include ethylenediaminetetraacetic acid (EDTA). For example, EDTA is added in a concentration of 1 mM or less. As an inhibitor for RNase, RNasin Plus Ribonuclease Inhibitor (available from Promega Corporation), Ribonuclease Inhibitor (available from Takara Bio Inc.), or RNase Inhibitor (available from TOYOBO CO., LTD.) may be used.

When the sample containing a nucleic acid contains DNA and RNA together, DNA and RNA can be separated by phenol-chloroform extraction. For example, RNA and DNA are separated into an aqueous layer and a chloroform layer, respectively, by phenol-chloroform extraction under an acidic condition. RNA and DNA are separated into an aqueous layer by phenol-chloroform extraction under a neutral condition. The kind of nucleic acid to be obtained can be selected by changing the condition as described above. The chloroform may be replaced by p-bromoanisole.

In the phenol-chloroform extraction, ISOGEN (registered trademark: available from NIPPON GENE CO., LTD.), TRIzol (registered trademark: available from Life Technologies Japan Ltd.), or 3D-Gene (registered trademark) RNA extraction reagent from liquid sample kit (available from Toray Industries, Inc.) may be used. In the aforementioned treatments, one process of the treatments may be carried out alone, or a process of different operation may be combined. The concentrations of the solutions used for the treatments may be changed, if necessary.

As the sample containing a nucleic acid, a solution in which a nucleic acid, an artificial nucleic acid, or a nucleic acid modified with a dye, phosphoric acid, or the like is dissolved can be used. When using the biological sample, a liquid sample such as a body fluid or a diluted solution thereof, or a diluted solution of a solid sample such as a cell pellet or a tissue fragment can be used. As the sample including the liquid sample or the solid sample, a solution obtained after any of the aforementioned treatments may be used as it is, or may be diluted, if necessary. A solution for dilution is not particularly limited. A solution generally used for the solution containing a nucleic acid such as water or a tris-hydrochloric acid buffer solution is preferably used. To the solution containing a nucleic acid, for example, guanidium chloride, guanidine thiocyanate, or urea may be added in a final concentration of 4 M or more.

The length of a nucleic acid to be collected is not particularly limited, and is preferably 1,000 base pairs or less. Pre-miRNA or miRNA of 300 base pairs or less can be collected at a high yield, which is hardly achieved by a conventional technology.

Example

Figure 1:
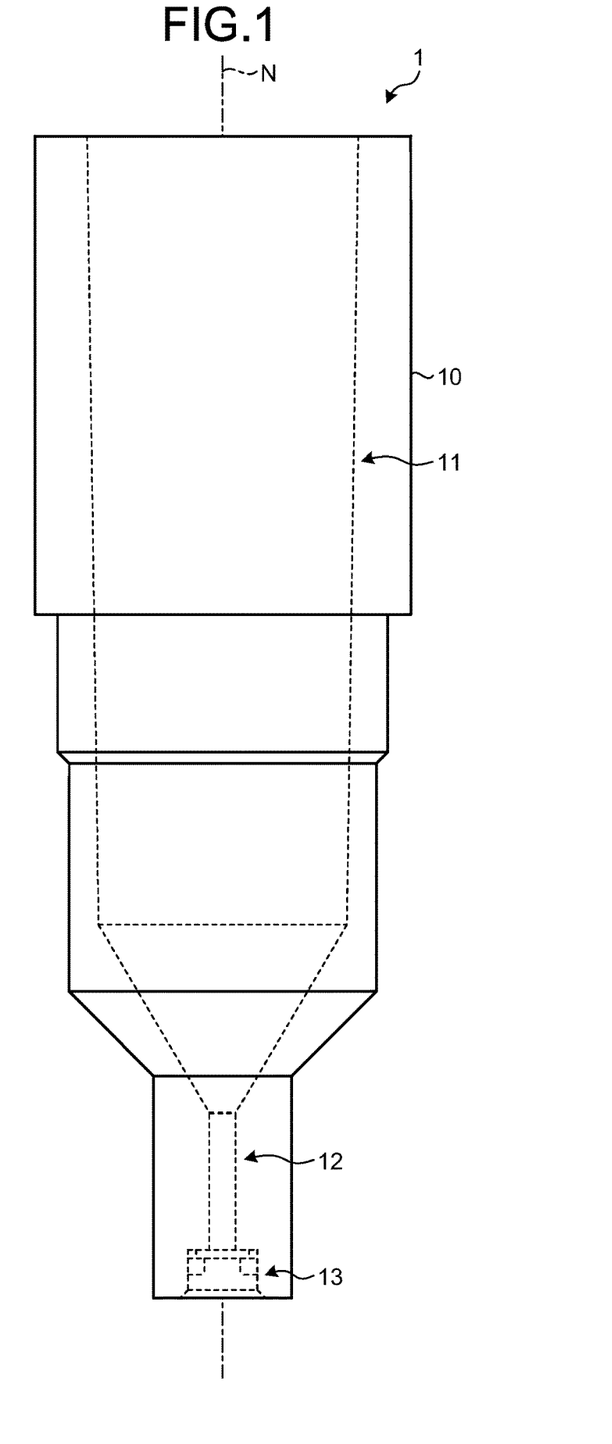
FIG. 1 is a plan view schematically illustrating a nucleic acid collection column according to one example.
Figure 2:
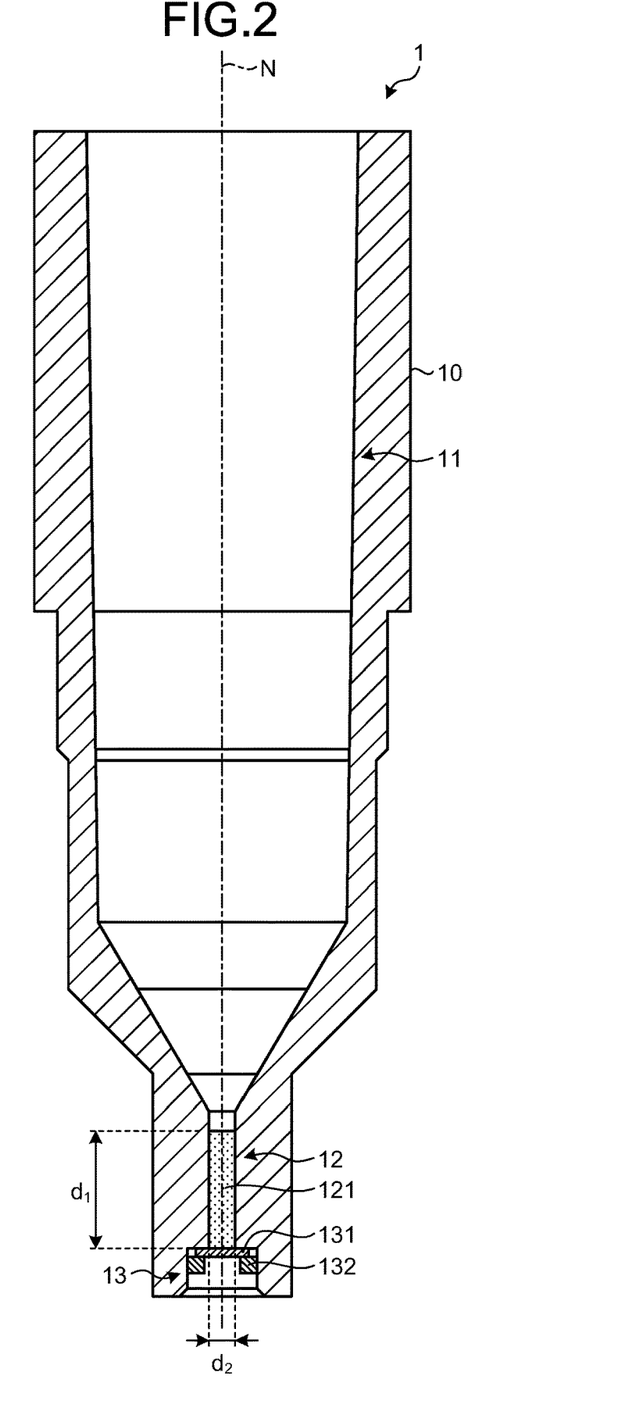
FIG. 2 is a cross-sectional view of the nucleic acid collection column illustrated in FIG. 1.

A nucleic acid collection column according to an example will be described with reference to FIGS. 1 and 2. FIG. 1 is a plan view schematically illustrating the nucleic acid collection column according to the example. FIG. 2 is a cross-sectional view of the nucleic acid collection column illustrated in FIG. 1. A nucleic acid collection column 1 illustrated in FIGS. 1 and 2 has a cylindrical body 10. Into the body 10, a biological sample is introduced. The body 10 has a hole that is capable of discharge. In this hole, a sample injection portion 11, a support adsorption portion 12, and a discharge portion 13 are disposed in this order from a side of introducing the biological sample.

The sample injection portion 11 has an opening to introduce a liquid sample containing a nucleic acid and a hole portion that is continuous to the support adsorption portion 12 in the body 10. The hole portion has a continuously decreased diameter at an end on a side of the support adsorption portion 12. The ratio of the volume of the sample injection portion 11 to the volume of the support adsorption portion 12 is preferably 100 or more and 10,000 or less.

The support adsorption portion 12 houses a plurality of supports 121 for adsorbing a nucleic acid that is contained in the sample. In the support adsorption portion 12, a space (hereinafter also referred to as "adsorption portion") that houses the supports 121 has a cylindrical shape having an axis parallel to a central axis N of the hole. For example, it is preferable that the volume of this space be 0.13 μL or more and 13.5 μL or less (the weight of the supports 121 be 0.1 mg or more and 10 mg or less).

It is preferable that the aspect ratio ($d_1/d_2$) of this space satisfy a relation of equation (1), where $d_1$ is the length (first length) in an axial direction of the space having the cylindrical shape, and $d_2$ is a diameter (second length) in a direction orthogonal to the axial direction (see FIG. 2). The length $d_1$ (first length) and the diameter $d_2$ (second length) extend in directions perpendicular to each other:

$$1.0 \leq d_1/d_2 < 15.0 \qquad (1).$$

1.0 that is the lower limit value of $d_1/d_2$ is a value determined based on a value when the collection rate of nucleic acid is 50% according to calculation. 15.0 that is the upper limit value of $d_1/d_2$ is a value determined based on a value when the biological sample, a washing solution, and an eluent are passed through the support adsorption portion 12 (between the supports 121) and discharged in the nucleic acid collection column 1. The aspect ratio more preferably satisfies $1.0 \le d_1/d_2 \le 14.0$.

The length $d_1$ is 1 mm or more and 10 mm or less. The diameter $d_2$ is 0.4 mm or more and 2 mm or less.

The shape of the space is not limited to the cylindrical shape and, for example, may be a prismatic shape. In the space that has the prismatic shape, the length corresponding to the diameter $d_2$ is a diameter of a circle circumscribed about this space.

The supports 121 include aluminum oxide having a surface where a water-soluble neutral polymer is adsorbed. The supports 121 have a diameter of particles (particle diameter or particle diameter) of 10 μm or more and 60 μm or less.

The neutral polymer is water-soluble, and the solubility thereof is at least 0.0001% by mass or more, preferably 0.001% by mass or more, more preferably 0.01% by mass or more, and further preferably 0.1% by mass or more.

A polymer represents a generic name for compounds in which a large number of repeating units, which are base units and are monomers, are connected. The polymer used for the supports 121 includes both a homopolymer consisting of one kind of monomer and a copolymer consisting of two or more kinds of monomers. Furthermore, the polymer includes a natural polymer and a synthetic polymer.

The neutral polymer is preferably a polymer having a zeta potential of −10 mV or more and +10 mV or less, more preferably −8 mV or more and +8 mV or less, further preferably −6 mV or more and +6 mV or less, and particularly preferably −4.0 mV or more and +1.1 V or less, in a solution with a pH of 7.

Specific examples of the neutral polymer include the following. For example, a polyvinyl-based polymer such as polyvinyl alcohol or polyvinyl pyrrolidone, a polyacrylamide-based polymer such as polyacrylamide, poly(N-isopropylacrylamide), or poly(N-(hydroxymethyl)acrylamide), a polyalkylene glycol-based polymer such as polyethylene glycol, polypropylene glycol, or polytetramethylene ether glycol, or a cellulose such as poly(2-ethyl-2-oxazoline), (hydroxypropyl)methylcellulose, methylcellulose, ethylcellulose, 2-hydroxyethylcellulose, or hydroxypropylcellulose can be used. A copolymer containing the aforementioned polymer can also be used.

The neutral polymer includes a polysaccharide such as ficoll, agarose, chitin, or dextran, or a polysaccharide analog, and a protein such as albumin, or peptide.

A portion of a functional group of the neutral polymer may be ionized or substituted with a functional group exhibiting positivity or negativity, or a functional group exhibiting water solubility such as an acetyl group may be introduced into a side chain.

For example, the neutral polymer preferably has a molecular weight of 0.4 kD or more, and more preferably 6 kD or more. The upper limit of the molecular weight of the neutral polymer is preferably 500 kD or less, and more preferably 150 kD or less. The molecular weight of the neutral polymer is preferably within a range of 0.4 kD or more and 500 kD or less, and more preferably 6 kD or more and 150 kD or less.

Aluminum oxide is an amphoteric oxide represented by a composition formula: $Al_2O_3$, also called alumina. Naturally generated aluminum oxide may be used, or industrially produced aluminum oxide may be used. Examples of a method of producing aluminum oxide include a Bayer process using gibbsite as a starting material, an alkoxide process through a hydroxide in a boehmite form (also called sol-gel process), a neutralization process, an oil droplet process, a thermal decomposition process of an aluminum salt, and an anode oxidation process. Aluminum oxide is classified into α-aluminum oxide, ρ-aluminum oxide, χ-aluminum oxide, κ-aluminum oxide, η-aluminum oxide, γ-aluminum oxide, δ-aluminum oxide, and θ-aluminum oxide, depending on a crystal structure thereof γ-aluminum oxide having a high specific surface area is preferred. Acidic sites ($Al^+$, $Al-OH_2^+$) and basic sites ($Al-O^-$) of aluminum oxide vary depending on the baking temperature during production. Depending on the number of acidic sites and basic sites of aluminum oxide, aluminum oxide is classified. When the number of acidic sites is large, aluminum oxide is acidic alumina. When the number of basic sites is large, aluminum oxide is basic alumina. When the number of acidic sites is substantially equal to the number of basic sites, aluminum oxide is neutral alumina. Any alumina can also be used.

It is preferable that aluminum oxide be granular. The particle diameters may be the same, or particles having different particle diameters may be mixed. For example, aluminum oxide having a particle diameter of less than 212 μm is preferably used, and aluminum oxide having a particle diameter of less than 100 μm is more preferably used. The particle diameter is defined by an aperture dimension of a sieve in accordance with Japanese Industrial Standards (JIS Z-8801-1:2006). For example, a particle that passes through a sieve having an aperture of 40 μm and does not pass through a sieve having an aperture of 32 μm in accordance with the JIS standard has a particle diameter of 32 μm or more and less than 40 μm.

As the supports 121, supports disclosed in International publication WO2016/152763 can be preferably used.

In the supports 121, the coverage of the neutral polymer on a surface of aluminum oxide is preferably 7% or more, more preferably 10% or more, further preferably 20% or more, particularly preferably 30% or more, and the most preferably 40% or more.

The discharge portion 13 discharges the biological sample that is passed through the support adsorption portion 12 to the outside. The diameter of an opening of the discharge portion 13 on the side of the support adsorption portion 12 is larger than the diameter of an opening of the support adsorption portion 12 on a side of the discharge portion 13.

In the discharge portion 13, a support-holding sheet 131 and a ring 132 are provided. The support-holding sheet 131 is provided at a boundary between the discharge portion 13 and the support adsorption portion 12, and covers an opening of the support adsorption portion 12 on the side of the discharge portion 13. The support-holding sheet 131 has a mesh shape that has a plurality of holes with a smaller diameter than the diameter of the supports 121. For example, the ring 132 is pressed into or fixed on an internal circumferential surface of the discharge portion 13, and prevents detachment of the support-holding sheet 131 from the discharge portion 13. Due to the support-holding sheet 131 provided, leakage of the supports 121 from the discharge portion 13 to the outside is prevented.

The support-holding sheet 131 may be subjected to a water-repellency treatment. Due to the water-repellency treatment, leakage of the sample containing a nucleic acid, the washing solution, and the eluent from the column can be prevented, and the flow rate of the column can be stabilized.

In the ring 132, it is preferable that the diameter (internal diameter) of the internal circumference be larger than the diameter of the opening of the support adsorption portion 12 on the side of the discharge portion 13. Specifically, the ratio of the internal diameter of the ring 132 to the diameter of the opening of the support adsorption portion 12 on the side of the discharge portion 13 is preferably 1 or more and 5 or less.

Figure 3:
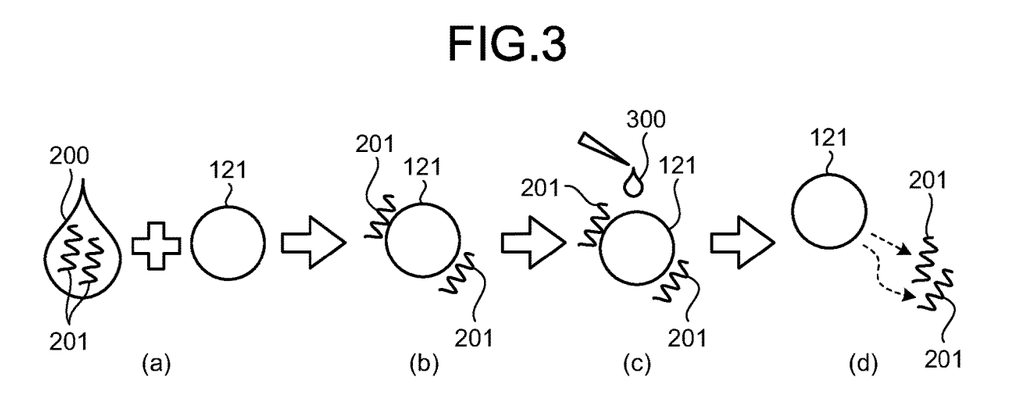
FIG. 3 is a view illustrating a method of collecting a nucleic acid.
Figure 4:
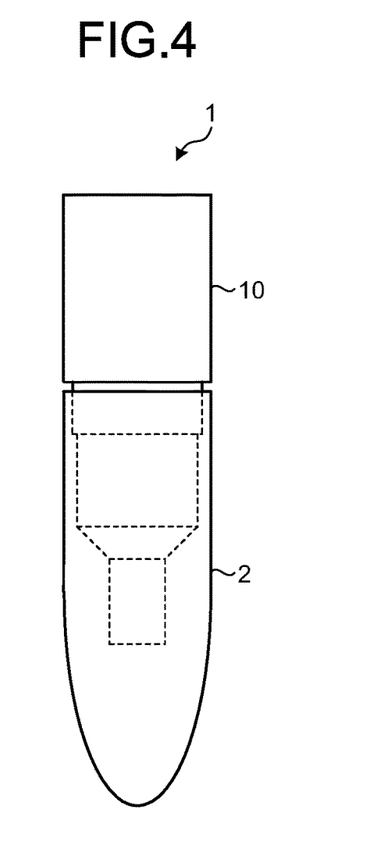
FIG. 4 is a view illustrating nucleic acid collection using the nucleic acid collection column according to the example.

In the example, a method of collecting a nucleic acid from the biological sample will be described with reference to FIGS. 3 and 4. FIG. 3 is a view illustrating the method of collecting a nucleic acid. FIG. 4 is a view illustrating nucleic acid collection using the nucleic acid collection column according to the example.

A sample 200 containing a nucleic acid 201 is mixed with the support 121 (see (a) of FIG. 3), to adsorb the nucleic acid 201 on the support 121 (see (b) of FIG. 3). In this example, it is preferable that the amount of the sample 200 containing the nucleic acid 201 in the nucleic acid collection column 1 that satisfies a condition of the aforementioned equation (1) be 100 μL or more and 20 mL or less. When the sample containing the nucleic acid is a liquid sample such as a body fluid, the sample may be introduced into the nucleic acid collection column as it is after sampling, or the sample may be diluted with a solution after sampling. When the sample containing the nucleic acid is a solid sample including a microorganism, a cell pellet, or a tissue fragment, the sample may be diluted with water or a buffer solution.

After the nucleic acid 201 is adsorbed on the support 121, the sample 200 containing a nucleic acid that is not adsorbed on the support 121 may be removed prior to shifting to the next operation. Specifically, by centrifugation with a container 2 attached to the nucleic acid collection column 1, the sample 200 containing the nucleic acid that is not adsorbed on the support 121 is shifted from the nucleic acid collection column 1 to the container 2, and the support 121 on which the nucleic acid 201 is adsorbed remains in the nucleic acid collection column 1.

Subsequently, the support 121 on which the nucleic acid 201 is adsorbed is cleaned with a washing solution 300 (see (c) of FIG. 3). Examples of the washing solution 300 include water, a 4-(2-hydroxyethyl)-1-piperazineethane sulfonic acid (HEPES, pH: 7) buffer solution, and a tris-hydrochloride buffer solution. By cleaning with the washing solution 300, a compound that is non-specifically adsorbed on the support 121 can be removed. To remove a protein, an ion, and a low-molecular-weight compound that are non-specifically adsorbed on the support 121, a surfactant may be added. To remove a protein that is non-specifically adsorbed on the support 121, a protease may be added. To isolate only DNA, a RNase may be added. In a washing treatment, the container 2 as illustrated in FIG. 4 is attached on a side of the discharge portion 13 of the nucleic acid collection column 1. By centrifugation with the container 2 attached to the nucleic acid collection column 1, the washing solution 300 is shifted from the nucleic acid collection column 1 to the container 2. The washing solution shifted to the container 2 contains the compound, the protein, and the RNA that are separated from the support 121.

Subsequently, an eluent is added to elute the nucleic acid 201 from the support 121. The amount of eluent introduced is preferably an amount that is 1.6 or more times and 8.5 or less times the volume of the space that houses the support 121 in the support adsorption portion 12. Specifically, the amount under the condition of the aforementioned equation (1) is preferably 2 μL or more and 30 μL or less. Also in an elution treatment, such a container 2 illustrated in FIG. 4 is newly attached. By centrifugation with the container 2 attached to the nucleic acid collection column 1, the eluent is shifted from the nucleic acid collection column 1 to the container 2. After the addition of the eluent, the nucleic acid collection column 1 is allowed to stand, or the eluent is heated. Thus, the elution can be enhanced. When the nucleic acid collection column is allowed to stand, the time is preferably within two hours. When the eluent is heated, the temperature is preferably 70° C. or lower, and more preferably 50° C. or lower. The eluent shifted to the container 2 contains the nucleic acid 201 eluted from the support 121. The collected nucleic acid 201 is used in a genetic test and the like. For example, a treatment under centrifugation conditions of 100 to 8,000 G and about one minute is preferred.

The eluent is not particularly limited as long as the nucleic acid 201 adsorbed on the support 121 can be eluted. The eluent is preferably a buffer solution. The buffer solution may contain a chelating agent. Specific examples of the buffer solution include a citrate buffer solution containing citric acid and sodium citrate, a phosphate buffer solution containing phosphoric acid and sodium phosphate, and a tris-EDTA buffer solution containing trishydroxyaminomethane and hydrochloric acid.

The pH of the buffer solution is preferably 4 or more and 9 or less, and more preferably 5 or more and 8 or less.

The adsorption ratio of the nucleic acid adsorbed on the support 121 can be determined as follows. The amount of the nucleic acid in the sample containing the nucleic acid is first calculated.

Examples of a process of determining the amount of the nucleic acid include measurement of absorbance, measurement of fluorescence, measurement of luminescence, electrophoresis, PCR, RT-PCR, analysis using a microarray, and analysis using a sequencer. When the nucleic acid is an unmodified nucleic acid, the absorbance of light with a wavelength of 260 nm can be measured to determine the amount of the nucleic acid. When the nucleic acid is a nucleic acid modified with a fluorescent dye, the fluorescence intensity based on the fluorescent dye can be compared with the fluorescence intensity in a solution of a known concentration, to determine the amount of the nucleic acid. Additionally, the amount of the nucleic acid can be determined by an electrophoresis process, in which a sample of a known concentration and a sample after nucleic acid collection are simultaneously migrated, a gel is dyed, and the concentrations of bands are compared by image processing.

The nucleic acid is adsorbed by the nucleic acid collection column 1, and the amount of the nucleic acid in the solution after adsorption is determined. This amount of the nucleic acid is the amount of the nucleic acid in the solution except for the adsorbed nucleic acid. Subsequently, a difference between the amount of the nucleic acid before adsorption and that after adsorption is determined. This difference is divided by the amount of the nucleic acid before adsorption, to obtain the adsorption ratio of the nucleic acid.

The elution ratio of the nucleic acid can be determined as follows. An eluent is first added to the support 121 on which the nucleic acid is adsorbed, and the amount of the nucleic acid in the solution after elution is determined. The amount of the nucleic acid corresponds to the elution amount of the nucleic acid. The elution amount of the nucleic acid is divided by the amount of the nucleic acid adsorbed on the support 121 (the amount of the nucleic acid after adsorption), to determine the elution ratio of the nucleic acid.

The collection rate of the nucleic acid is the product of the adsorption ratio and the elution ratio of the nucleic acid. The collection rate calculated by the aforementioned process is the same as the value obtained by dividing the elution amount of the nucleic acid by the amount of the nucleic acid before adsorption.

With our method, high adsorption ratio and elution ratio can be obtained even when the eluent in a small amount of 2 μL or more and 30 μL or less is used for the sample in a small amount of 100 μL or more and 20 mL or less, as described above. The collection rate calculated by multiplying the adsorption ratio by the elution ratio is also increased. As a specific example of our method, genome analysis in which 300 μL of blood is collected, a nucleic acid is collected from the blood as a sample containing the nucleic acid, and a disease such as cancer is specified can be assumed.

According to the aforementioned example, the nucleic acid collection column 1 to adsorb a nucleic acid has a configuration in which the aspect ratio $(d_1/d_2)$ of the space housing the support 121 satisfies the relation of equation (1) $(1.0 \leq d_1/d_2 < 15.0)$. Therefore, the volume of the column can be decreased compared to the conventional configuration to increase the collection of the eluent and to decrease the volume of the eluent. When a nucleic acid is collected by using the nucleic acid collection column 1, the sensitivity of the column for collecting a nucleic acid can be increased, and the nucleic acid can be collected with high efficiency.

EXAMPLES

Hereinafter, details of collection columns and methods will be described by Examples. This disclosure is, however, not interpreted to be limited to Examples.
Materials
Polymer to be adsorbed on aluminum oxide: polyethylene glycol (available from Merck Ltd.)
Aluminum oxide: γ-aluminum oxide (N613N: available from JGC Catalysts and Chemicals Ltd.)
Sodium polyphosphate (CAS No. 68915-31-1: available from FUJIFILM Wako Pure Chemical Corporation)
Nucleic acid: Cy3-DNA synthesized by Cy3-labeling a 5'-terminal of "let7a" (22 bases) known as miRNA was used.
Mixer: CUTE MIXER CM-1000 (available from TOKYO RIKAKIKAI CO., LTD.)
Centrifugal separator: CT15RE (available from Hitachi, Ltd.)
Human serum: From a healthy subject, a human serum was collected with venoject II vacuum blood collection tube VP-AS109K60 (available from Terumo Corporation).
Production of Support
10 mg of aluminum oxide was weighed and placed in a 1.5-mL tube. As an aqueous polymer solution, 100 μL of 10 wt % polyethylene glycol (PEG, molecular weight: 10 kD) that was a water-soluble neutral polymer was added to this tube, and stirred for 10 minutes by a mixer. After stirring, each column was filled with this solution as a solution containing a support, to produce a spin column filled with the support. At that time, the volume of the filled support corresponded to a support-housing space of a nucleic acid collection column used in each of Examples and Comparative Examples.
Nucleic Acid Collection Treatment
As the solution containing a nucleic acid, 200 μL of human serum containing 25 pmol of Cy3-DNA was used. 600 μL of solution of 7 M guanidine thiocyanate (GTN) and 25 mM (4-(2-hydroxyethyl)-1-piperazineethanesulfonic acid (HEPES, pH: 7), and 200 μL of the human serum were mixed by pipetting, and added to a nucleic acid collection column filled with the support, followed by centrifugation (200 G, 15 minutes). A collection tube (corresponding to the aforementioned container 2) was then exchanged.

Subsequently, 700 μL of 0.1% Tween 20-25 mM HEPES buffer solution (pH: 7) was added as a washing solution to the nucleic acid collection column, followed by centrifugation (1,000 G, 2 minutes). A collection tube was then exchanged. This operation was further repeated again.

5 μL of 125 mM phosphoric acid-125 mM polyphosphoric acid mixed solution (pH: 7) was added to the nucleic acid collection column, and allowed to stand for 15 minutes. Subsequently, centrifugation (1,000 G, 2 minutes) was carried out, and a flow-through was collected as a nucleic acid collection solution.
Adsorption Ratio Calculation Processing
The adsorption ratio was calculated by fluorescence measurement of Cy3 as follows.

The fluorescence intensity of the mixed solution containing 25 pmol of Cy3-DNA, of 600 μL of 7 M GTN-25 mM HEPES (pH: 7) solution and 200 μL of human serum before addition to the nucleic acid collection column filled with the support was first measured.

The fluorescence intensity of the flow-through solution (nucleic acid collection solution) of the nucleic acid collection column was then measured.

The fluorescence intensity after passage through the nucleic acid collection column was divided by the fluorescence intensity before passage through the nucleic acid collection column, and the obtained value was multiplied by the amount of the nucleic acid (25 pmol) before introduction into the nucleic acid collection column to obtain the amount of nucleic acid in the flow-through solution.

A difference between the amount of the nucleic acid (25 pmol) before passage through the nucleic acid collection column and this value was obtained, and the amount of the adsorbed nucleic acid was calculated. The amount of the adsorbed nucleic acid was divided by the amount of the nucleic acid (25 pmol) before adsorption on the support to calculate the adsorption ratio.
Elution Ratio Calculation Processing
The elution ratio was calculated by fluorescence measurement of Cy3 as follows.

To the support on which the nucleic acid was adsorbed, 5 μL of 125 mM phosphoric acid-125 mM polyphosphoric acid mixed solution (pH: 7) was first added, 95 μL of water was added to an eluent after elution, and fluorescence measurement was carried out.

Subsequently, 5 μL of 125 mM phosphoric acid-125 mM polyphosphoric acid mixed solution (pH: 7) in which 25 pmol of Cy3-DNA was dissolved was prepared, and 95 μL of water added to prepare a reference solution. The reference solution was subjected to fluorescence measurement.

The fluorescence intensity of the eluent was divided by the fluorescence intensity of the reference solution, and the amount of the eluted nucleic acid calculated. The amount of the eluted nucleic acid was divided by the amount of the adsorbed nucleic acid to calculate the elution ratio.
Collection Rate Calculation Processing
The collection rate was calculated by multiplying the obtained adsorption ratio by the elution ratio.

Example 1

Using a nucleic acid collection column having a space (adsorption portion) that housed a support (particle) having a particle diameter of 20 μm or more and 32 μm or less, and had a diameter (corresponding to $d_2$ described above) of 1.60 mm, a length (corresponding to $d_1$ described above) of 6.0 mm, an aspect ratio $(d_1/d_2)$ of 3.75, and a volume (a volume of the space housing the support) of 12.56 μL, a nucleic acid was collected in 20 μL of eluent. The configuration of the nucleic acid collection column and the like of Example 1, and the adsorption ratio, elution ratio, and collection rate of a nucleic acid are listed in Table 1.

TABLE 1

| | Particle diameter [μm] | Elution volume [μL] | Adsorption portion ||| Adsorption ratio [%] | Elution ratio [%] | Collection rate [%] |
|---|---|---|---|---|---|---|---|---|
| | | | Volume [μL] | Aspect ratio | Diameter [mm] | Length [mm] | | | |
| Example 1 | 20 to 32 | 20 | 12.56 | 3.75 | 1.60 | 6.0 | 99.4 | 69.0 | 68.6 |
| Example 2 | 20 to 32 | 10 | 5.02 | 12.50 | 0.80 | 10.0 | 99.7 | 57.3 | 57.1 |
| Example 3 | 20 to 32 | 5 | 1.51 | 3.75 | 0.80 | 3.0 | 95.3 | 90.4 | 86.2 |
| Example 4 | 20 to 32 | 5 | 0.13 | 2.50 | 0.40 | 1.0 | 86.1 | 96.0 | 83.0 |
| Example 5 | 20 to 32 | 5 | 0.28 | 1.67 | 0.60 | 1.0 | 99.6 | 79.8 | 79.5 |
| Example 6 | 20 to 32 | 5 | 0.50 | 1.25 | 0.80 | 1.0 | 85.2 | 92.9 | 79.1 |
| Example 7 | 20 to 32 | 5 | 0.79 | 1.00 | 1.00 | 1.0 | 54.4 | 94.1 | 51.2 |

Example 2

Using a nucleic acid collection column having an adsorption portion that housed a support having a particle diameter of 20 μm or more and 32 μm or less, and had a diameter of 0.80 mm, a length of 10.0 mm, an aspect ratio of 12.50, and a volume 5.02 μL, a nucleic acid was collected in 10 μL of eluent. The configuration of the nucleic acid collection column and the like of Example 2, and the adsorption ratio, elution ratio, and collection rate of a nucleic acid are listed in Table 1.

For supports (particles) of Examples 2 to 7, a particle diameter of 20 μm or more and 32 μm or less was utilized similarly to Example 1.

Example 3

Using a nucleic acid collection column having an adsorption portion that housed a support having a particle diameter of 20 μm or more and 32 μm or less, and had a diameter of 0.80 mm, a length of 3.0 mm, an aspect ratio of 3.75, and a volume of 1.51 μL, a nucleic acid was collected in 5 μL of eluent. The configuration of the nucleic acid collection column and the like of Example 3, and the adsorption ratio, elution ratio, and collection rate of a nucleic acid are listed in Table 1.

Example 4

A nucleic acid was collected in the same manner as in Example 3 except that a nucleic acid collection column having an adsorption portion having a diameter of 0.40 mm, a length of 1.0 mm (an aspect ratio of 2.50), and a volume of 0.13 μL was used. The configuration of the nucleic acid collection column and the like of Example 4, and the adsorption ratio, elution ratio, and collection rate of a nucleic acid are listed in Table 1.

Example 5

A nucleic acid was collected in the same manner as in Example 3 except that a nucleic acid collection column having an adsorption portion having a diameter of 0.60 mm, a length of 1.0 mm (an aspect ratio of 1.67), and a volume of 0.28 μL was used. The configuration of the nucleic acid collection column and the like of Example 5, and the adsorption ratio, elution ratio, and collection rate of a nucleic acid are listed in Table 1.

Example 6

A nucleic acid was collected in the same manner as in Example 3 except that a nucleic acid collection column having an adsorption portion having a diameter of 0.80 mm, a length of 1.0 mm (an aspect ratio of 1.25), and a volume of 0.50 μL was used. The configuration of the nucleic acid collection column and the like of Example 6, and the adsorption ratio, elution ratio, and collection rate of a nucleic acid are listed in Table 1.

Example 7

A nucleic acid was collected in the same manner as in Example 3 except that a nucleic acid collection column having an adsorption portion having a diameter of 1.00 mm, a length of 1.0 mm (an aspect ratio of 1.00), and a volume of 0.79 μL was used. The configuration of the nucleic acid collection column and the like of Example 7, and the adsorption ratio, elution ratio, and collection rate of a nucleic acid are listed in Table 1.

Example 8

Using a nucleic acid collection column having an adsorption portion that housed a support having a particle diameter of 32 μm or more and 45 μm or less, and had a diameter of 0.40 mm, a length of 1.0 mm, an aspect ratio of 2.50, and a volume of 0.13 μL, a nucleic acid was collected in 5 μL of eluent. The configuration of the nucleic acid collection column and the like of Example 8, and the adsorption ratio, elution ratio, and collection rate of a nucleic acid are listed in Table 2.

TABLE 2

| | Particle diameter [μm] | Elution volume [μL] | Adsorption portion ||| Adsorption ratio [%] | Elution ratio [%] | Collection rate [%] |
|---|---|---|---|---|---|---|---|---|
| | | | Volume [μL] | Aspect ratio | Diameter [mm] | Length [mm] | | | |
| Example 8 | 32 to 45 | 5 | 0.13 | 2.50 | 0.40 | 1.0 | 80.1 | 86.0 | 69.6 |
| Example 9 | 32 to 45 | 10 | 5.02 | 12.50 | 0.80 | 10.0 | 99.8 | 77.1 | 76.9 |

Example 9

Using a nucleic acid collection column having an adsorption portion that housed a support having a particle diameter of 32 μm or more and 45 μm or less, and had a diameter of 0.80 mm, a length of 10.0 mm, an aspect ratio of 12.50, and a volume of 5.02 μL, a nucleic acid was collected in 10 μL of eluent. The configuration of the nucleic acid collection column and the like of Example 9, and the adsorption ratio, elution ratio, and collection rate of a nucleic acid are listed in Table 2.

Comparative Example 1

Using a nucleic acid collection column having an adsorption portion that housed a support having a particle diameter of 20 μm or more and 32 μm or less, and had a diameter of 5.8 mm, a length of 0.5 mm, an aspect ratio of 0.09, and a volume of 13.20 μL, a nucleic acid was collected in 20 μL of eluent. The configuration of the nucleic acid collection column and the like of Comparative Example 1, and the adsorption ratio, elution ratio, and collection rate of a nucleic acid are listed in Table 3.

Comparative Example 2

Using a nucleic acid collection column having an adsorption portion that housed a support having a particle diameter of 20 μm or more and 32 μm or less, and had a diameter of 0.8 mm, a length of 0.5 mm, an aspect ratio of 0.63, and a volume of 0.25 μL, a nucleic acid was collected in 5 μL of eluent. The configuration of the nucleic acid collection column and the like of Comparative Example 2, and the adsorption ratio, elution ratio, and collection rate of a nucleic acid are listed in Table 3.

For supports (particles) of Comparative Examples 2 to 5, a particle diameter of 20 μm or more and 32 μm or less was utilized similarly to Comparative Example 1.

Comparative Example 3

Using a nucleic acid collection column having an adsorption portion that housed a support having a particle diameter of 20 μm or more and 32 μm or less, and had a diameter of 0.6 mm, a length of 0.5 mm, an aspect ratio of 0.83, and a volume of 0.06 μL, a nucleic acid was collected in 5 μL of eluent. The configuration of the nucleic acid collection column and the like of Comparative Example 3, and the adsorption ratio, elution ratio, and collection rate of a nucleic acid are listed in Table 3.

Comparative Example 4

Using a nucleic acid collection column having an adsorption portion that housed a support having a particle diameter of 20 μm or more and 32 μm or less, and had a diameter of 2.0 mm, a length of 8.0 mm, an aspect ratio of 4.00, and a volume of 25.1 μL, a nucleic acid was collected in 20 μL of eluent. The configuration of the nucleic acid collection column and the like of Comparative Example 4, and the adsorption ratio, elution ratio, and collection rate of a nucleic acid are listed in Table 3.

Comparative Example 5

Using a nucleic acid collection column having an adsorption portion that housed a support having a particle diameter of 20 μm or more and 32 μm or less, and had a diameter of 7.5 mm, a length of 1.5 mm, an aspect ratio of 0.20, and a volume of 68.0 μL, a nucleic acid was collected in 20 μL of eluent. The configuration of the nucleic acid collection column and the like of Comparative Example 5, and the adsorption ratio, elution ratio, and collection rate of a nucleic acid are listed in Table 3.

TABLE 3

| | Particle Particle diameter [μm] | Elution volume [μL] | Adsorption portion Volume [μL] | Adsorption portion Aspect ratio | Adsorption portion Diameter [mm] | Adsorption portion Length [mm] | Adsorption ratio [%] | Elution ratio [%] | Collection rate [%] |
|---|---|---|---|---|---|---|---|---|---|
| Comparative Example 1 | 20 to 32 | 20 | 13.20 | 0.09 | 5.8 | 0.5 | 31.2 | 67.2 | 21.0 |
| Comparative Example 2 | 20 to 32 | 5 | 0.25 | 0.63 | 0.8 | 0.5 | 36.4 | 95.4 | 34.7 |
| Comparative Example 3 | 20 to 32 | 5 | 0.06 | 0.83 | 0.6 | 0.5 | 44.2 | 96.9 | 42.8 |
| Comparative Example 4 | 20 to 32 | 20 | 25.1 | 4.00 | 2.0 | 8.0 | 99.3 | 38.9 | 38.6 |
| Comparative Example 5 | 20 to 32 | 20 | 68.0 | 0.20 | 7.5 | 1.5 | 99.7 | 20.5 | 20.4 |

When using the nucleic acid collection columns of Examples 1 to 9, all the collection rates are 50% or more. In Comparative Examples 1 to 5, all the collection rates are lower than 45%, which are lower than those in Examples 1 to 9. These results indicate that an aspect ratio ($d_1/d_2$) outside 0.1 or more and less than 15.0 or a volume outside 0.13 μL or more and 13.5 μL or less decreases the adsorption ratio or elution ratio of the nucleic acid, resulting in a decrease in collection rate.

Subsequently, a nucleic acid was collected by a nucleic acid collection column having a discharge portion 13 with an opening of different size. The size of the opening of the discharge portion 13 was adjusted by changing the internal diameter of a ring 132 described above.

Example 10

A nucleic acid was collected in the same manner as in Example 3 except that the diameter of an outlet opening was changed to 0.5 mm. The configuration of the nucleic acid collection column and the like of Example 10, and the adsorption ratio, elution ratio, and collection rate of a nucleic acid are listed in Table 4. Provided that the diameter of the outlet opening in Example 3 was 1.00 mm.

TABLE 4

|  | Particle Particle Diameter [μm] | Elution volume [μl] | Adsorption portion | | | Outlet opening diameter [mm] | Adsorption ratio [%] | Elution ratio [%] | Collection rate [%] |
|---|---|---|---|---|---|---|---|---|---|
|  |  |  | Volume [μl] | Aspect ratio | Diameter [mm] | Length [mm] |  |  |  |
| Example 10 | 20 to 32 | 5 | 1.5 | 3.75 | 0.80 | 3.00 | 0.50 | 91.0 | 85.3 | 77.6 |
| Example 11 | 32 to 45 | 5 | 1.5 | 3.75 | 0.80 | 3.00 | 1.00 | 91.7 | 90.3 | 82.8 |
| Example 12 | 32 to 45 | 5 | 1.5 | 3.75 | 0.80 | 3.00 | 0.50 | 86.5 | 76.3 | 66.0 |

Example 11

Using a nucleic acid collection column having an adsorption portion that housed a support having a particle diameter of 32 μm or more and 45 μm or less, and had a diameter of 0.80 mm, a length of 3.00 mm, an aspect ratio of 3.75, a volume of 1.5 μL, and a discharge portion 13 having a ring 132 with an internal diameter (diameter of an outlet opening) of 1.00 mm, a nucleic acid was collected in 5 μL of eluent. The configuration of the nucleic acid collection column and the like of Example 11, and the adsorption ratio, elution ratio, and collection rate of a nucleic acid are listed in Table 4.

Example 12

A nucleic acid was collected in the same manner as in Example 11 except that the diameter of an outlet opening was changed to 0.5 mm. The configuration of the nucleic acid collection column and the like of Example 12, and the adsorption ratio, elution ratio, and collection rate of a nucleic acid are listed in Table 4.

In Examples 10 to 12, all the collection rates are more than 65%. In a comparison of Example 3 to Example 10, as the diameter of the outlet opening is larger, the collection rate is higher. Similarly, in a comparison of Example 11 to Example 12, as the diameter of the outlet opening is larger, the collection rate is higher. The results indicate that the outlet opening with a larger diameter enables collection of a nucleic acid at a higher collection rate.

Liquid Delivery Test 1 mL of water or serum was added to a nucleic acid collection column equipped with a container on a side of a discharge portion, and centrifuged at 200 G. For one sample, the liquid delivery amount was measured every centrifugation time. The amount of water or serum that was passed through the nucleic acid collection column and transferred to the container was measured at each centrifugation time. In the liquid delivery test, the used nucleic acid collection column housed a support having a particle diameter of 20 μm or more and 32 μm or less. An aspect ratio described below represents the ratio of the diameter of a space (corresponding to the support adsorption portion 12) for housing the support to the length thereof.

Example 13

To a nucleic acid collection column having a space (support adsorption portion) having a diameter of 0.8 mm, a length of 8 mm, and an aspect ratio of 10, 1 mL of water was added, and the liquid delivery amount was measured with change of centrifugation time (liquid delivery time). The configuration of the nucleic acid collection column of Example 13, and the liquid delivery amount (mL) are listed in Table 5.

TABLE 5

|  | Diameter [mm] | Length [mm] | Aspect ratio | Time [min] | | | | | | | |
|---|---|---|---|---|---|---|---|---|---|---|---|
|  |  |  |  | 0 | 2 | 4 | 6 | 8 | 10 | 12 | 15 |
| Example 13 | 0.8 | 8 | 10 | 0 | 0.27 | 0.5 | 0.69 | 0.81 | 1 | 1 | 1 |
| Example 14 | 0.8 | 10 | 12.5 | 0 | 0.27 | 0.49 | 0.68 | 0.8 | 1.01 | 1.01 | 1.01 |
| Example 15 | 0.8 | 12 | 15 | 0 | 0.24 | 0.45 | 0.6 | 0.73 | 0.86 | 0.97 | 0.97 |

Example 14

To a nucleic acid collection column having a space (support adsorption portion) having a diameter of 0.8 mm, a length of 10 mm, and an aspect ratio of 12.5, 1 mL of water was added, and the liquid delivery amount was measured with change of centrifugation time (liquid delivery time). The configuration of the nucleic acid collection column of Example 14, and the liquid delivery amount (mL) are listed in Table 5.

Example 15

To a nucleic acid collection column having a space (support adsorption portion) having a diameter of 0.8 mm, a length of 12 mm, and an aspect ratio of 15, 1 mL of water was added, and the liquid delivery amount was measured with change of centrifugation time (liquid delivery time). The configuration of the nucleic acid collection column of Example 15, and the liquid delivery amount (mL) are listed in Table 5.

Example 16

To a nucleic acid collection column having a space (support adsorption portion) having a diameter of 0.8 mm, a length of 8 mm, and an aspect ratio of 10, 1 mL of serum was added, and the liquid delivery amount was measured with change of centrifugation time (liquid delivery time). The configuration of the nucleic acid collection column of Example 16, and the liquid delivery amount (mL) are listed in Table 6.

TABLE 6

| | Diameter [mm] | Length [mm] | Aspect ratio | Time [min] | | | | | | | | Note |
|---|---|---|---|---|---|---|---|---|---|---|---|---|
| | | | | 0 | 2 | 4 | 6 | 8 | 10 | 15 | 30 | |
| Example 16 | 0.8 | 8 | 10 | 0 | 0.16 | 0.36 | 0.5 | 0.81 | 1.02 | 1.02 | 1.02 | |
| Example 17 | 0.8 | 10 | 12.5 | 0 | 0.16 | 0.32 | 0.47 | 0.74 | 1 | 1 | 1 | |
| Comparative Example 6 | 0.8 | 12 | 15 | 0 | 0.13 | 0.25 | 0.29 | 0.41 | 0.44 | 0.47 | 0.47 | (Liquid delivery was stopped) |

Example 17

To a nucleic acid collection column having a space (support adsorption portion) having a diameter of 0.8 mm, a length of 10 mm, and an aspect ratio of 12.5, 1 mL of serum was added, and the liquid delivery amount was measured with change of centrifugation time (liquid delivery time). The configuration of the nucleic acid collection column of Example 17, and the liquid delivery amount (mL) are listed in Table 6.

Comparative Example 6

To a nucleic acid collection column having a space (support adsorption portion) having a diameter of 0.8 mm, a length of 12 mm, and an aspect ratio of 15, 1 mL of serum was added, and the liquid delivery amount was measured with change of centrifugation time (liquid delivery time). The configuration of the nucleic acid collection column of Comparative Example 6, and the liquid delivery amount (mL) are listed in Table 6.

In all Examples 13 to 17, the almost whole amount of water or serum introduced into the nucleic acid collection column was delivered by centrifugation at 200 G for 10 minutes. In Comparative Example 6, liquid delivery was stopped by 8-minute centrifugation. These results indicate that when the aspect ratio is more than 15, the liquid delivery of serum is stopped on the way, and the whole amount of serum cannot be transferred.

INDUSTRIAL APPLICABILITY

According to our nucleic acid collection column, a nucleic acid can be collected with high efficiency by adjusting the aspect ratio of a space housing a support. Since a nucleic acid can be collected with high efficiency, our collection columns is industrially very applicable.

The invention claimed is:

1. A nucleic acid collection column for collecting a nucleic acid from a liquid sample containing the nucleic acid, comprising:
    a sample injection portion having an opening into which the liquid sample containing the nucleic acid is injected;
    a support adsorption portion configured to house a support that adsorbs the nucleic acid, the nucleic acid being adsorbed on the support in the support adsorption portion; and
    a discharge portion configured to discharge a liquid passed through the support adsorption portion, wherein
    the support includes aluminum oxide having a surface where a water-soluble neutral polymer is adsorbed,
    a space that houses the support in the support adsorption portion has a cylindrical shape, and has a volume of 0.13 μL or more and 13.5 μL or less, and
    an aspect ratio ($d_1/d_2$) of the space satisfies $1.0 \leq d_1/d_2 < 15.0$, where $d_1$ is a length in an axial direction of the space, and $d_2$ is a diameter in a direction orthogonal to the axial direction.

2. The nucleic acid collection column according to claim 1, wherein
    the discharge portion includes a support-holding sheet configured to hold the support housed in the support adsorption portion, and a ring fixing the support-holding sheet, and
    the ring has an internal diameter larger than a diameter of an opening of the support adsorption portion on a side of the discharge portion.

3. The nucleic acid collection column according to claim 1, wherein the support has a particle diameter of 10 μm or more and 60 μm or less.

* * * * *